(12) United States Patent
Elder

(10) Patent No.: US 9,759,713 B2
(45) Date of Patent: Sep. 12, 2017

(54) HAND-HELD TEST METER WITH TEST STRIP SIMULATION PASSIVE CIRCUIT BLOCK

(71) Applicant: LifeScan Scotland Limited, Inverness (GB)

(72) Inventor: David Elder, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 389 days.

(21) Appl. No.: 14/446,485

(22) Filed: Jul. 30, 2014

(65) Prior Publication Data

US 2016/0033439 A1 Feb. 4, 2016

(51) Int. Cl.
*G01N 27/327* (2006.01)
*G01N 33/487* (2006.01)
*G01N 27/416* (2006.01)

(52) U.S. Cl.
CPC ... *G01N 33/48785* (2013.01); *G01N 27/3273* (2013.01); *G01N 27/3272* (2013.01); *G01N 27/3274* (2013.01); *G01N 27/4163* (2013.01)

(58) Field of Classification Search
None
See application file for complete search history.

(56) References Cited

U.S. PATENT DOCUMENTS

| 3,661,748 | A | * | 5/1972 | Blackmer | G01N 27/404 204/401 |
| 5,124,661 | A | * | 6/1992 | Zelin | G01R 31/2829 324/439 |
| 7,263,501 | B2 | * | 8/2007 | Tirinato | G06Q 10/087 360/27 |
| 2007/0084734 | A1 | | 4/2007 | Roberts et al. | |

(Continued)

FOREIGN PATENT DOCUMENTS

| EP | 1012602 A1 | 6/2000 |
| EP | 1241475 A2 | 9/2002 |

(Continued)

OTHER PUBLICATIONS

Combined Search and Examination Report issued in Application No. GB13036165, Jul. 2, 2013; 7 pages.

*Primary Examiner* — Luan Van
*Assistant Examiner* — Steven E Rosenwald

(57) ABSTRACT

A hand-held test meter for use with an electrochemical-based analytical test strip in the determination of an analyte in a bodily fluid sample includes a housing, a micro-controller disposed in the housing, a test strip simulation passive circuit block disposed in the housing, and a strip port connector ("SPC") configured to operationally receive an electrochemical-based analytical test. The test strip simulation passive circuit block is in electrical communication with the SPC and the SPC is configured in electrical communication with the micro-controller. In addition, the test strip simulation passive circuit block is configured to simulate (Continued)

insertion of an electrochemical-based analytical test strip into the SPC and also to simulate application of a bodily fluid sample to an electrochemical-based analytical test strip inserted into the SPC by presenting one or both of (i) an alternating current (AC) load to SPC; and (ii) a direct current (DC) load to the SPC.

8 Claims, 6 Drawing Sheets

(56) References Cited

U.S. PATENT DOCUMENTS

| | | | |
|---|---|---|---|
| 2007/0087397 A1 | 4/2007 | Kraft et al. | |
| 2009/0119047 A1* | 5/2009 | Zelin | G01K 3/04 |
| | | | 702/82 |
| 2014/0326614 A1* | 11/2014 | Guthrie | G01N 27/307 |
| | | | 205/775 |

FOREIGN PATENT DOCUMENTS

| | | | | |
|---|---|---|---|---|
| GB | 2521481 A | * 12/2013 | | G01N 27/327 |
| WO | 92/01947 | 2/1992 | | |
| WO | 99/00667 | 1/1999 | | |
| WO | 00/49942 | 8/2000 | | |
| WO | 2009/036429 A2 | 3/2009 | | |
| WO | 2010/049669 A1 | 5/2010 | | |

* cited by examiner

HAND-HELD TEST METER WITH TEST STRIP SIMULATION PASSIVE CIRCUIT BLOCK

BACKGROUND OF THE INVENTION

Field of the Invention

The present invention relates, in general, to medical devices and, in particular, to test meters and related methods.

Description of Related Art

The determination (e.g., detection and/or concentration measurement) of an analyte in, or characteristic of, a bodily fluid sample is of particular interest in the medical field. For example, it can be desirable to determine glucose, ketone bodies, cholesterol, lipoproteins, triglycerides, acetaminophen, hematocrit and/or HbA1c concentrations in a sample of a bodily fluid such as urine, blood, plasma or interstitial fluid. Such determinations can be achieved using a hand-held test meter in combination with analytical test strips (e.g., electrochemical-based analytical test strips).

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings, in which like numerals indicate like elements, of which:

DETAILED DESCRIPTION OF ILLUSTRATIVE EMBODIMENTS

Figure 1:
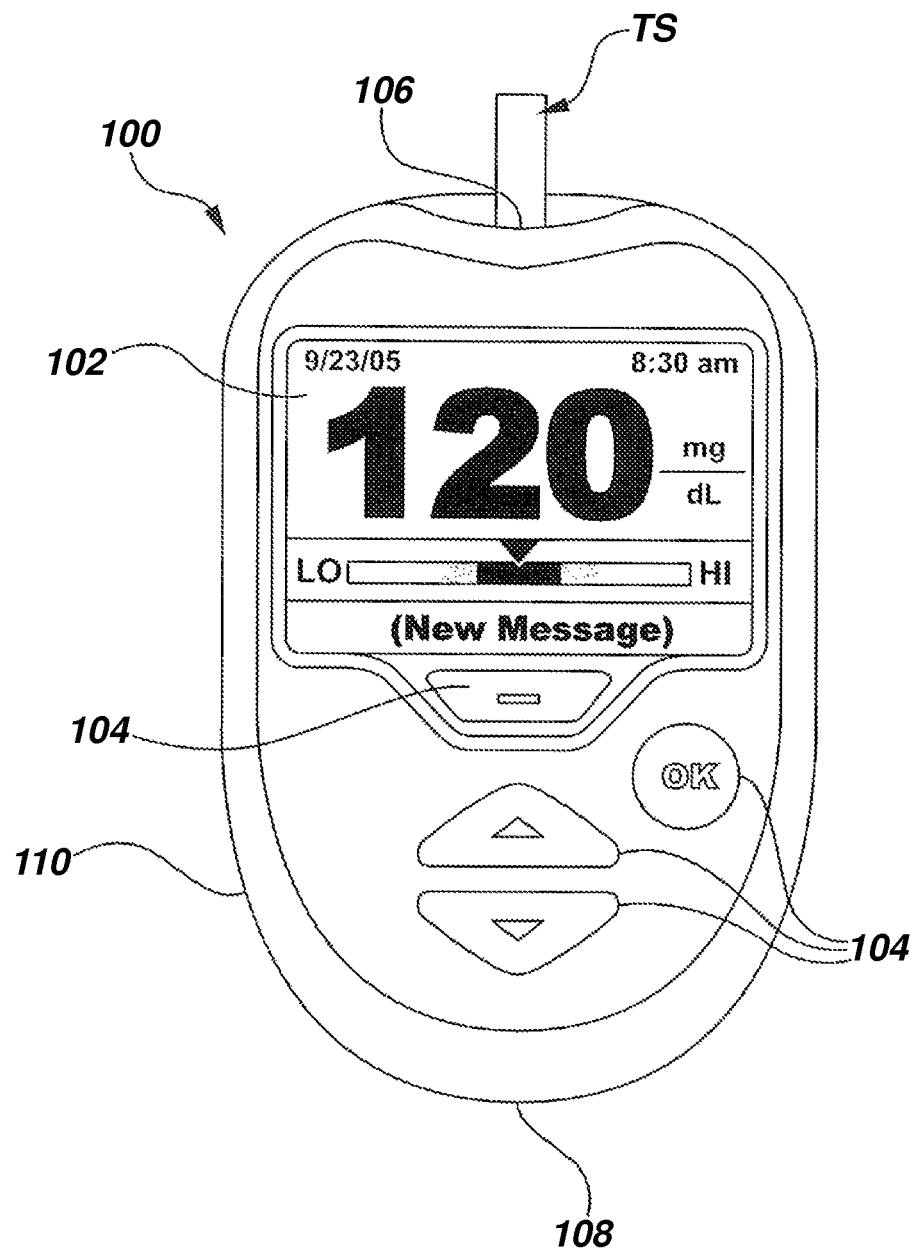
FIG. 1 is a simplified depiction of a hand-held test meter according to an embodiment of the present invention.

The following detailed description should be read with reference to the drawings, in which like elements in different drawings are identically numbered. The drawings, which are not necessarily to scale, depict exemplary embodiments for the purpose of explanation only and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention.

As used herein, the terms "about" or "approximately" for any numerical values or ranges indicate a suitable dimensional tolerance that allows the part or collection of components to function for its intended purpose as described herein.

In general, hand-held test meters for use with an electrochemical-based analytical test strip in the determination of an analyte in, and/or a characteristic of, a bodily fluid sample according to embodiments of the present invention include a housing, a micro-controller disposed in the housing, a test strip simulation passive circuit block disposed in the housing, and a strip port connector configured to operationally receive the electrochemical-based analytical test strip. Moreover, the test strip simulation passive circuit block is in electrical communication with the strip port connector and the strip port connector is configured in electrical communication with the micro-controller. In addition, the test strip simulation passive circuit block is configured to simulate insertion of an electrochemical-based analytical test strip into the strip port connector and/or to simulate application of a bodily fluid sample to an electrochemical-based analytical test strip inserted into the strip port connector. The simulation is accomplished by presenting one or both of (i) an alternating current (AC) load to the strip port connector; and (ii) a direct current (DC) load to the strip port connector.

Hand-held test meters according to embodiments of the present invention are beneficial in that the test strip simulation passive circuit block includes only relatively inexpensive passive circuit elements such as mechanical switches, resistors, capacitors, and diodes (e.g., a Schotkky diode). In addition, such hand-held test meters are beneficial in that the test strip simulation passive circuit block can be employed to easily and repeatedly test operation of the hand-held test meter without the need for, or the variation induced by, an actual electrochemical-based analytical test strip and a control solution that mimics a bodily fluid sample. Moreover, the test strip simulation passive circuit block can also be employed to demonstrate use of the hand-held test meter and to diagnose suspected operational failures of hand-held test meters.

Once one skilled in the art is apprised of the present disclosure, he or she will recognize that an example of a hand-held test meter that can be readily modified as a hand-hand test meter according to the present invention is the commercially available OneTouch® Ultra® 2 glucose meter from LifeScan Inc. (Milpitas, Calif.). Additional examples of hand-held test meters that can also be modified are found in U.S. Patent Application Publications No's. 2007/0084734 (published on Apr. 19, 2007) and 2007/0087397 (published on Apr. 19, 2007) and in International Publication Number WO2010/049669 (published on May 6, 2010), each of which is hereby incorporated herein in full by reference.

Figure 2:
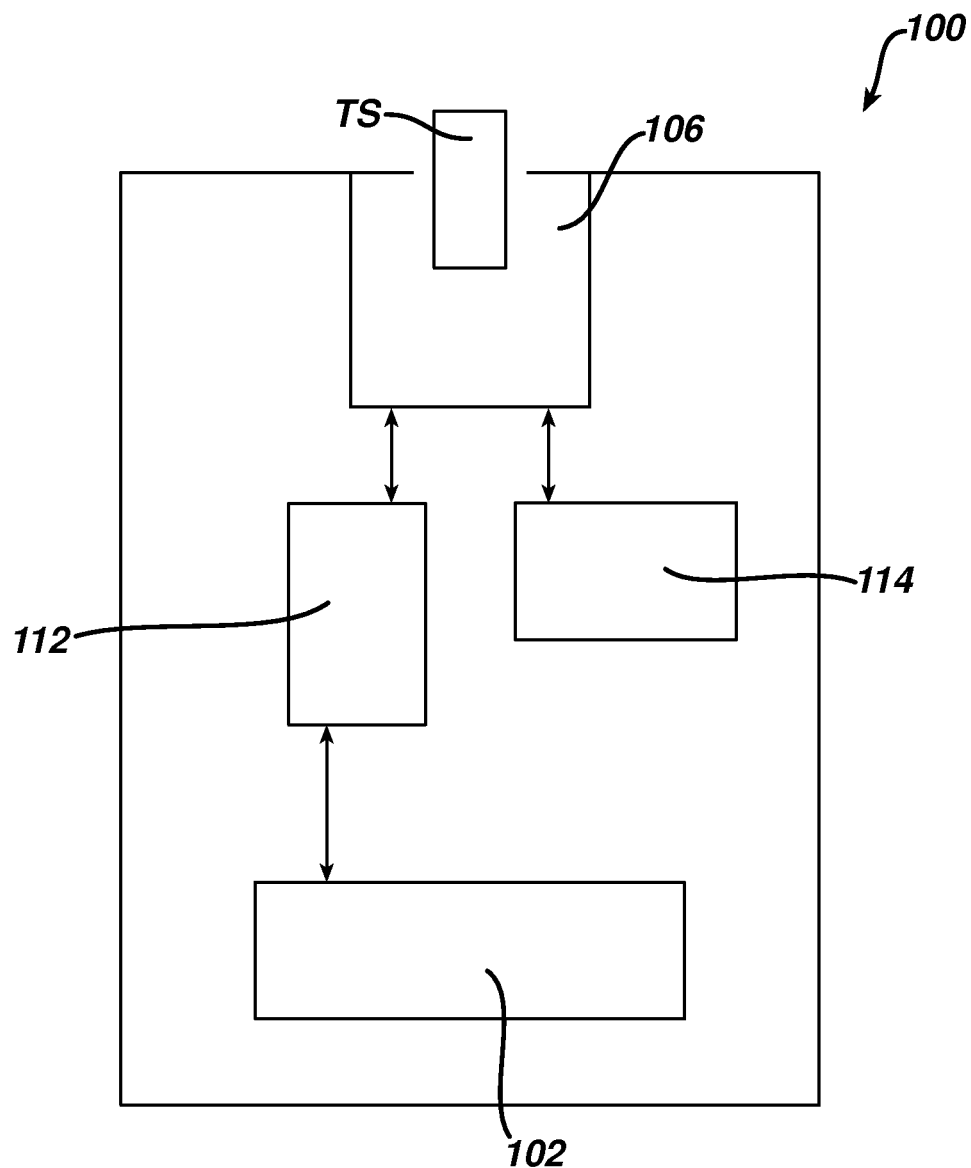
FIG. 2 is a simplified block diagram of various blocks of the hand-held test meter of FIG. 1.

FIG. 1 is a simplified depiction of a hand-held test meter 100 for the determination of an analyte in a bodily fluid sample according to an embodiment of the present invention. FIG. 2 is a simplified block diagram of various blocks of hand-held test meter 100.

Referring to FIGS. 1 and 2, hand-held test meter 100 includes a display 102, a plurality of user interface buttons 104, a strip port connector 106, a USB interface 108, and a housing 110 (see FIG. 1). Referring to FIG. 2 in particular, hand-held test meter 100 also includes a micro-controller block 112, a test strip simulation passive circuit block 114, and other electronic components (not shown) for applying an electrical bias (e.g., an alternating current (AC) and/or direct current (DC) bias) to an electrochemical-based analytical test strip (labeled TS in FIGS. 1 and 2), and also for measuring an electrochemical response (e.g., plurality of test current values) and determining an analyte or characteristic based on the electrochemical response. To simplify the current descriptions, the figures do not depict all such electronic circuitry.

Display 102 can be, for example, a liquid crystal display or a bi-stable display configured to show a screen image. An example of a screen image during the determination of an analyte in a bodily fluid sample may include a glucose concentration, a date and time, an error message, and a user interface for instructing a user how to perform a test. Examples of screen images during use of the test strip simulation passive circuit block may be an image reporting electrochemical-based analytical test strip insertion test complete, glucose concentration test complete, or a simulation error message.

Strip port connector 106 is configured to operatively interface with an electrochemical-based analytical test strip TS, such as an electrochemical-based analytical test strip configured for the determination of hematocrit and/or glucose in a whole blood sample. Therefore, the electrochemical-based analytical test strip is configured for operative insertion into strip port connector 106 and to operatively interface with micro-controller block 112 via, for example, suitable electrical contacts, wires, electrical interconnects or other structures known to one skilled in the art.

USB Interface 108 can be any suitable interface known to one skilled in the art. USB Interface 108 is an electrical component that is configured to power and provide a data line to hand-held test meter 100.

Micro-controller block 112 also includes a memory sub-block that stores suitable algorithms for the determination of an analyte based on the electrochemical response of an analytical test strip and to also determine a characteristic (e.g., hematocrit) of the introduced bodily fluid sample. Micro-controller block 112 is disposed within housing 110 and can include any suitable micro-controller and/or micro-processer known to those of skill in the art. Suitable micro-controllers include, but are not limited to, micro-controllers available commercially from Texas Instruments (Dallas, Tex., USA) under the MSP430 series of part numbers; from STMicroelectronics (Geneva, Switzerland) under the STM32F and STM32L series of part numbers; and Atmel Corporation (San Jose, Calif., USA) under the SAM4L series of part numbers).

Test strip simulation passive circuit block 114 is in electrical communication with strip port connector 106 (see FIG. 2). Typically, test strip simulation passive circuit block is configured to be connected and disconnected from electrical contacts of a strip port connector via a user operable switch(es) of the test strip simulation passive circuit block. Further descriptions of such electrical communication and the inclusion of switches in the test strip simulation passive circuit block are provided with respect to FIGS. 3-6 described below.

Moreover, test strip simulation passive circuit block 114 is configured to simulate insertion of an electrochemical-based analytical test strip into the strip port connector and to simulate application of a bodily fluid sample to an electrochemical-based analytical test strip inserted into the strip port connector by presenting at least one of (i) an alternating current (AC) load to the strip port connector; and (ii) a direct current (DC) load to the strip port connector. A DC load can be presented using, for example, a resistor network and/or a parallel resistor and capacitor network. An AC load can be presented, for example, using a suitable RC (resistor-capacitor) network and/or RC network combined with a diode(s). Moreover and in general, diodes can be included in test strip simulation passive circuit blocks included in embodiments of the present invention to provide a transient response to a change in DC bias. The AC and/or DC load presented to the strip port connector responds to an electrical bias (e.g., an alternating current (AC) and/or direct current (DC) bias) from other components of the hand-held test meter (such as the micro-controller) in a manner that simulates test strip insertion and/or application of a bodily fluid sample to an inserted electrochemical-based analytical test strip. Further detailed examples of test strip simulation passive circuit blocks and their interconnection to strip port connectors are provided herein with respect to the embodiments of FIGS. 3, 4, 5 and 6.

As is described below with respect to FIG. 3-5, test strip simulation passive circuit blocks employed in embodiments of the present invention can include at least one switch and at least one passive circuit component (such as a diode, capacitor, and/or resistor). Moreover, the strip port connector of hand-held test meters according to embodiments of the present invention includes at least, a first electrical contact, and a second electrical contact with the test strip simulation passive circuit block being in electrical communication with the first electrical contact and second electrical contact when the appropriate switch(es) of the test strip simulation passive circuit block are in a closed configuration.

Figure 3:
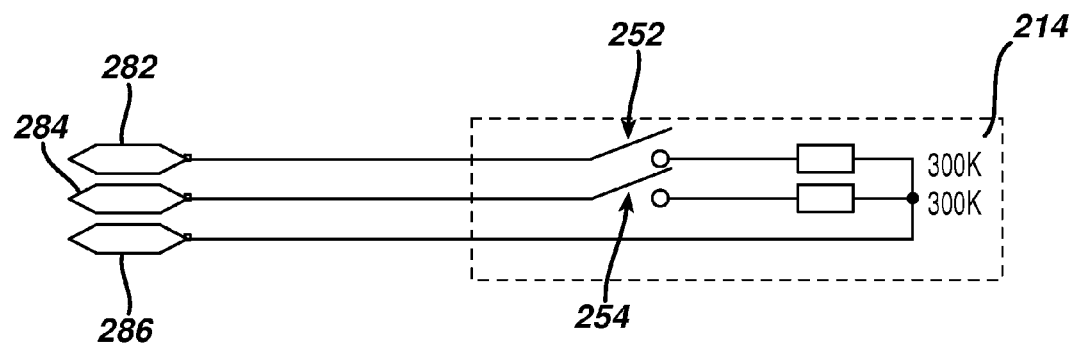
FIG. 3 is a simplified schematic diagram of a test strip simulation passive circuit block, as can be employed in embodiments of hand-held test meters of the present invention, connected to a first electrical contact, a second electrical contact and a third electrical contact of a hand-held test meter.
Figure 4:
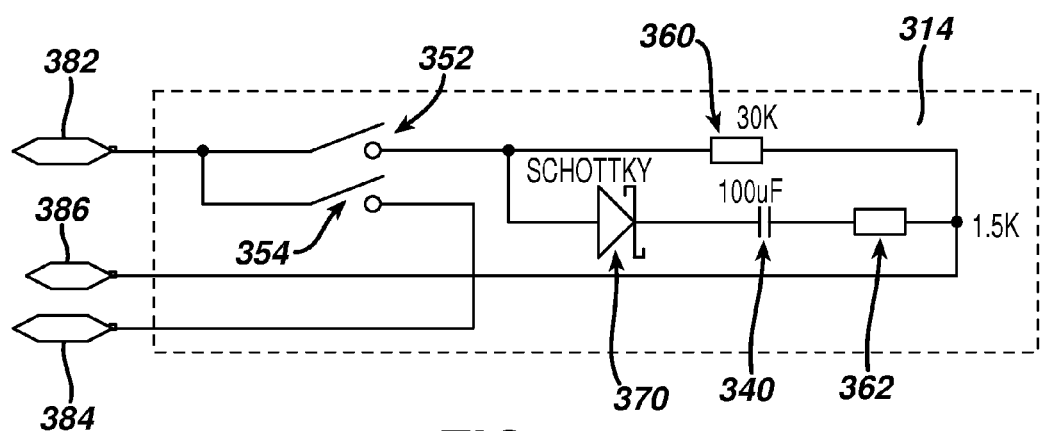
FIG. 4 is a simplified schematic diagram of another test strip simulation passive circuit block, as can be employed in embodiments of hand-held test meters of the present invention, connected to a first electrical contact, a second electrical contact and a third electrical contact of a hand-held test meter.

Once apprised of the present invention, one of skill in the art will recognize that hand-held test meters according to the present invention can include any suitable number of electrical contacts including, for example, three electrical contacts (i.e., a first electrical contact, a second electrical contact and a third electrical contact) as depicted in FIGS. 3 and 4. In addition, and if desired, test strip simulation passive circuit blocks employed in embodiments of the present invention can include an electronic switch (such an analog electronic switch or relay switch) but are still referred to as "passive" since such an electronic switch would be configured to connect an otherwise passive network (circuit) of, for example, resistors, capacitors and/or diodes, to a strip port connector.

Moreover, the test strip simulation passive circuit block can be configured to simulate insertion of an electrochemical-based analytical test strip into the strip port connector and to simulate application of a bodily fluid sample to an electrochemical-based analytical test strip inserted into the strip port connector by providing at least one of (i) an alternating current (AC) load to the first electrical contact and the second electrical contact; and (ii) a direct current (DC) load to the first electrical contact and second electrical contact upon closing of the at least one switch. Moreover, the test strip simulation passive circuit block can be configured to be at least partially disconnected from the first electrical contact, and second electrical contact upon opening of the at least one switch.

FIG. 3 is a simplified schematic diagram of a test strip simulation passive circuit block 214 (demarcated by the dashed lines of FIG. 3), as can be employed in embodiments of hand-held test meters of the present invention, connected to a first electrical contact 282, a second electrical contact 284 and a third electrical contact 286 of a strip port connector (not depicted in FIG. 3) of a hand-held test meter (also not depicted in FIG. 3).

Test strip simulation passive circuit block 214 includes first switch 252, second switch 254, first resistor 260 (i.e., a 300K ohm resistor) and second resistor 262 (also a 300K ohm resistor). First electrical contact 282 can be, for example, an electrical contact configured for connection to a first working electrode of an electrochemical-based analytical test strip. Second electrical contact 284 can be, for example, an electrical contact configured for connection to a second working electrode of an electrochemical-based analytical test strip. Third electrical contact 286 can be, for example, an electrical contact configured for connection to a reference electrode of an electrochemical-based analytical test strip. Although first resistor 260 and second resistor 262 are depicted in FIG. 3 as 300K ohm resistors, the value of such resistors can be predetermined to simulate various types of bodily fluid samples applied to an analytical test strip. The various types of bodily fluid sample can include, for example, whole blood samples of various blood glucose concentrations. Any suitable resistors can be employed in the test strip simulation passive circuit blocks of hand-held test meters according to the present invention including resistors available commercially from, for example, Vishay Intertechnology (Malvern, Pa., USA).

Test strip simulation passive circuit block 214 is configured such that simultaneous closure of switches 252 and 254 "activates" test strip simulation passive circuit block 214 and presents a resistive load to the first, second and third electrical contacts 282, 284 and 286. The resistive load simulates application of a bodily fluid sample (e.g., a whole blood sample of predetermined glucose concentration) to an electrochemical-based analytical test strip inserted into the strip port connector. It should be noted that the embodiment depicted in FIG. 3 does not simulate insertion of an electrochemical-based analytical test strip into the strip port connector.

FIG. 4 is a simplified schematic diagram of another test strip simulation passive circuit block 314 (demarcated by the dashed lines of FIG. 4), as can be employed in embodiments of hand-held test meters of the present invention, connected to a first electrical contact 382, a second electrical contact 384 and a third electrical contact 386 of a hand-held test meter.

Test strip simulation passive circuit block 314 includes first switch 352, second switch 354, first resistor 360 (i.e., a 30K ohm resistor) and second resistor 262 (also a 1.5K ohm resistor), a Schottky diode 370 and a capacitor 340 (i.e., a 100 micro-Farad capacitor). First electrical contact 382 can be, for example, an electrical contact configured for connection to a first working electrode of an electrochemical-based analytical test strip. Second electrical contact 384 can be, for example, an electrical contact configured for analytical test strip detection. Third electrical contact 386 can be, for example, an electrical contact configured for connection to a reference electrode of an electrochemical-based analytical test strip. Schottky diode 370 can be any suitable Schottky diode including, for example, a Schottky diode commercially available as part number BAT54 from Fairchild Semiconductor (San Jose, Calif., USA).

Test strip simulation passive circuit block 314 is configured such that closure of switch 354 "activates" test strip simulation passive circuit block 314 and simulates electrochemical-based analytical test strip insertion. The test strip insertion is simulating by providing an electrical circuit for a small DC current (i.e., a DC current of less than 30 micro-amps) from other components of the hand-held test meter to flow between first electrical contact 382 and second electrical contact 384. The closure of switch 352 simulates sample application by presenting a load (and a resulting passive negative current pulse) to the first, second and third electrical contacts 382, 384 and 386 for a period of 4 seconds to 5 seconds. The current pulse is an exponential decay pulse with a peak of around −400 micro-amps and is the result of an electrical signal from the hand-held meter that produces a stepped DC bias through the test strip simulation passive circuit block that, in turn, creates the current pulse.

Figure 5:
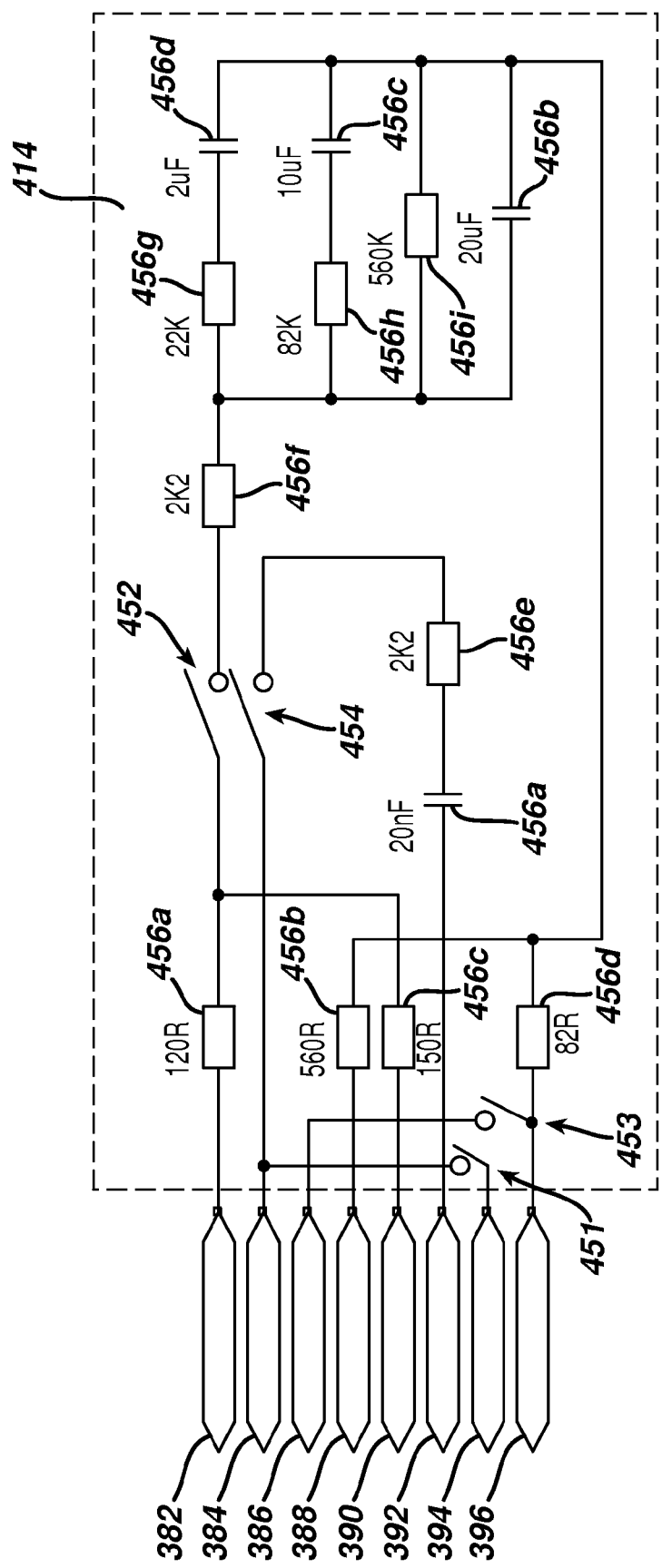
FIG. 5 is a simplified schematic diagram of a further test strip simulation passive circuit block, as can be employed in embodiments of hand-held test meters of the present invention, connected to eight electrical contacts of a hand-held test meter.
Figure 6:
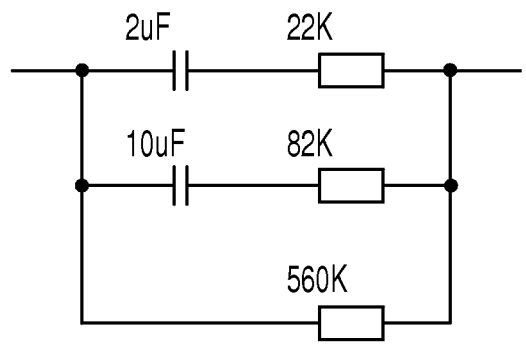
FIG. 6 is a simplified schematic of a portion of the test strip simulation passive circuit block of FIG. 5.
Figure 7:
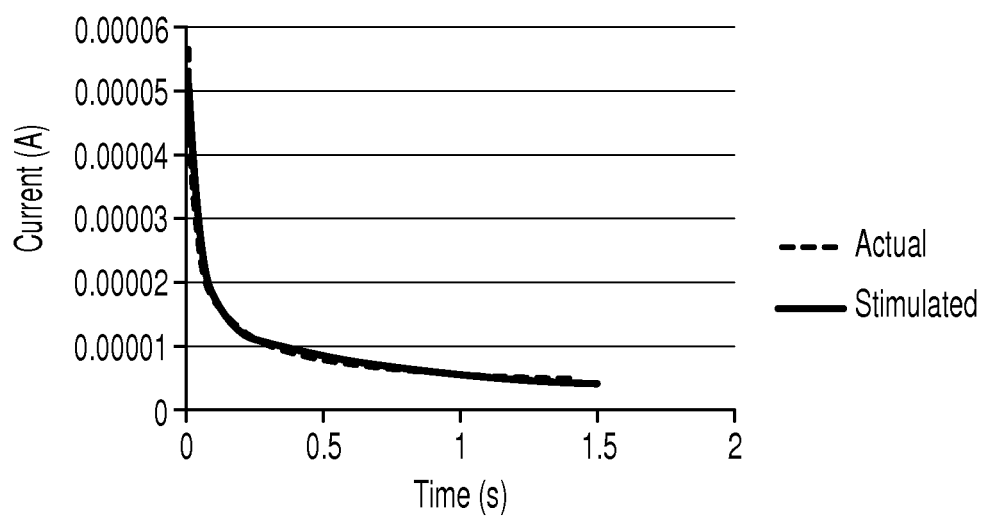
FIG. 7 is a simplified graph of current versus time for (i) data collected from an electrochemical-based analytical test strip following the application of a bodily fluid sample thereto; and (ii) collected using the test strip simulation passive circuit block portion of FIG. 6.

FIG. 5 is a simplified schematic diagram of a further test strip simulation passive circuit block 414 (demarcated by the dashed lines of FIG. 5), as can be employed in embodiments of hand-held test meters of the present invention, connected to eight electrical contacts of a hand-held test meter. FIG. 6 is a simplified schematic of a portion of test strip simulation passive circuit block 414. FIG. 7 is a simplified graph of current versus time for (i) data collected from an electrochemical-based analytical test strip following the application of a bodily fluid sample thereto; and (ii) collected using the test strip simulation passive circuit block portion of FIG. 6.

Test strip simulation passive circuit block 414 is connected to a first electrical contact 382, a second electrical contact 384, a third electrical contact 386, a fourth electrical contact 388, a fifth electrical contact 390, a sixth electrical contact 392, a seventh electrical contact 394 and an eighth electrical contact 396 of a strip port connector (not depicted in FIG. 5) of a hand-held test meter (also not depicted in FIG. 5).

Test strip simulation passive circuit block 414 includes first switch 451, second switch 452, third switch 453, fourth switch 454, nine resistors (456a through 456i) and four capacitors (458a through 458d).

Test strip simulation passive circuit block 414 is configured such that simultaneous closure of switches 451, 452, 453 and 454 "activates" test strip simulation passive circuit block 414 and simulates electrochemical-based analytical test strip insertion and sample application. In the embodiment of FIG. 5, closure of switch 454 simulates fill detection of an inserted electrochemical-based analytical test strip rather than the simple insertion of an analytical test strip. In other words, closure of switch 454 simulates insertion of a filled electrochemical-based analytical test strip. Closure of switches 451 and 453 simulates the simple insertion of an electrochemical-based analytical test strip. Closure of switch 452 presents both an AC and DC load based simulation of sample application to an electrochemical-based analytical test strip. Resistors 456a. 456b, 456c and 456d are configured to simulate electrochemical-based analytical test strip trace resistances.

FIG. 6 depicts a portion of the test strip simulation passive circuit block 414 consisting of two parallel RC (resistor-capacitor) networks and an offset resistor. FIG. 7 compares a test meter's measured response upon being presented with the DC load of the partial circuit in FIG. 6 versus an actual test meter response during the determination of glucose in a whole blood sample. FIG. 7 indicates that the electrical circuit of FIG. 6 (created entirely of passive components) results in a response that is nearly identical to that of an actual electrochemical-based analytical test strip following the application of a whole blood sample. The data of FIG. 7 that is labeled "simulated" was generated using a hand-held meter bias of 450 milli-volts applied to test strip simulation passive circuit block of FIG. 6.

Figure 8:
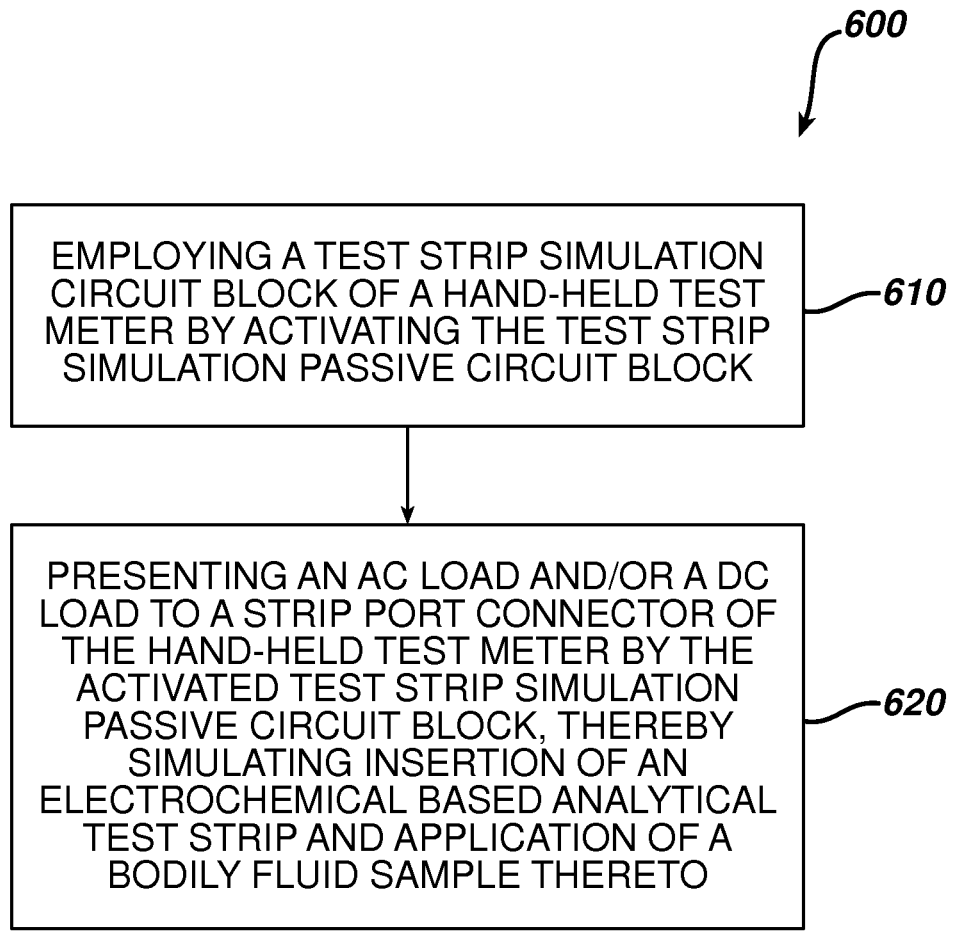
FIG. 8 is a flow diagram depicting stages in a method for operating a hand-held test meter according to an embodiment of the present invention.

FIG. 8 is a flow diagram depicting stages in a method 600 for employing a hand-held test meter (e.g., hand-held test meter 100 of FIG. 1) for use with an electrochemical-based analytical test strip for the determination of an analyte in, or a characteristic of, a bodily fluid sample, according to an embodiment of the present invention. Method 600 includes employing a test strip simulation passive circuit block of a hand-held test meter by activating the test strip simulation passive circuit block (see step 610 of FIG. 8).

At step 620 of method 600, upon activation of the test strip simulation passive circuit block, at least one of an alternating current (AC) load and a direct current (DC) load are presented to the strip port connector by the test strip simulation passive circuit block. The at least one of an AC load and a DC load are predetermined to simulate at least one of insertion of an electrochemical-based analytical test strip into the strip port connector and/or application of a bodily fluid sample to the simulated inserted electrochemical-based analytical test strip.

Once apprised of the present disclosure, one skilled in the art will recognize that methods according to embodiments of the present invention, including method 600, can be readily modified to incorporate any of the techniques, benefits and characteristics of hand-held test meters according to embodiments of the present invention and described herein.

Once apprised of the present disclosure, one skilled in the art will recognize that the meters and methods according to embodiments of the present invention, including method 600, can employ any suitable electrochemical techniques, including those based on Cottrell current measurements, coulometry, amperometry, chronoamperometry, potentiometry, and chronopotentiometry.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that devices and methods within the scope of these claims and their equivalents be covered thereby.

What is claimed is:

1. A hand-held test meter for use with an electrochemical-based analytical test strip in the determination of an analyte in a bodily fluid sample, the hand-held test meter comprising:

a housing;

a micro-controller disposed in the housing;

a test strip simulation passive circuit block disposed in the housing; and a strip port connector configured to operationally receive an electrochemical-based analytical test strip;

wherein the test strip simulation passive circuit block is in electrical communication with the strip port connector; and wherein the test strip simulation passive circuit block is configured to simulate at least one of insertion of an electrochemical-based analytical test strip into the strip port connector and application of a bodily fluid sample to an electrochemical-based analytical test strip inserted into the strip port connector by presenting at least one of:

an alternating current (AC) load to the strip port connector; and a direct current (DC) load to the strip port connector; and wherein strip port connector is configured in electrical communication with the micro-controller.

2. The hand-held test meter of claim 1 wherein the test strip simulation passive circuit block includes:

at least one switch; and at least one passive circuit component;

and wherein the a strip port connector includes at least:

a first electrical contact; and a second electrical contact;

wherein the test strip simulation passive circuit block is in electrical communication with the first electrical contact and second electrical contact when the at least one electrical switch is in a closed configuration; and wherein the test strip simulation passive circuit block is configured to simulate insertion of an electrochemical-based analytical test strip into the strip port connector and to simulate application of a bodily fluid sample to an electrochemical-based analytical test strip inserted into the strip port connector by providing at least one of:

an alternating current (AC) load to the first electrical contact and the second electrical contact upon closing of the at least one switch; and a direct current (DC) load to the first electrical contact and second electrical contact upon closing of the at least one switch;

wherein the test strip simulation passive circuit block is configured to be at least partially disconnected from the first electrical contact and second electrical contact upon opening of the at least one electrical switch; and wherein the first electrical contact and second electrical contact are configured in electrical communication with the micro-controller.

3. The hand-held test meter of claim 1 wherein the ac load is presented using a parallel resistor and capacitor network of the test strip simulation passive circuit block.

4. The hand-held test meter of claim 1 wherein the at least one of an ac load and a dc load is presented using a resistor network of the test strip simulation passive circuit block.

5. The hand-held test meter of claim 1 wherein the dc load is presented using a parallel resistor/capacitor (RC) and offset resistor network.

6. The hand-held test meter of claim 1 wherein the test strip simulation passive circuit block includes at least one of a resistor, a capacitor and a Schottky diode.

7. The hand-held test meter of claim 1 wherein the test strip simulation passive circuit block includes a first switch and a second switch.

8. The hand-held test meter of claim 1 wherein the electrochemical-based analytical test strip is an electrochemical-based analytical test strip configured for the determination of glucose in a whole blood bodily fluid sample.

* * * * *